United States Patent

Choy et al.

[11] Patent Number: 6,010,994
[45] Date of Patent: *Jan. 4, 2000

[54] LIQUID COMPOSITIONS CONTAINING N-ALKYL AMMONIUM ACETONITRILE SALTS

[75] Inventors: Clement K. Choy, Alamo; James E. Deline, Livermore; Lafayette D. Foland, Dublin; Aram Garabedian, Jr., Fremont; Kevin A. Klotter, Livermore; Michael J. Petrin, Antioch; Martin J. Phillippi; William L. Smith, both of Pleasanton, all of Calif.

[73] Assignee: The Clorox Company, Oakland, Calif.

[*] Notice: This patent is subject to a terminal disclaimer.

[21] Appl. No.: 08/758,540

[22] Filed: Nov. 29, 1996

Related U.S. Application Data

[63] Continuation-in-part of application No. 08/475,292, Jun. 7, 1995, Pat. No. 5,739,327.

[51] Int. Cl.[7] .............................. C11D 3/39; C11D 3/395; C11D 1/62; C09K 3/00

[52] U.S. Cl. .............. 510/312; 252/186.39; 252/186.38; 544/86; 544/163; 544/402; 546/246; 510/329

[58] Field of Search .................... 252/186.39, 186.38; 510/312, 329; 544/86, 163, 402; 546/246

[56] References Cited

U.S. PATENT DOCUMENTS

| | | | |
|---|---|---|---|
| 2,425,693 | 8/1947 | Cook et al. | 558/459 |
| 2,489,950 | 11/1949 | Blicke | 546/205 |
| 2,625,547 | 1/1953 | Lawson et al. | 544/171 |

(List continued on next page.)

FOREIGN PATENT DOCUMENTS

| | | |
|---|---|---|
| 0303520 | 8/1988 | European Pat. Off. . |
| 883075582 | 8/1988 | European Pat. Off. . |
| A20303520 | 8/1988 | European Pat. Off. . |

(List continued on next page.)

OTHER PUBLICATIONS

Hart, William F. et al., Some New Quaternary—Substituted alkyl Morpholinium chlorides and Pyrrolidinium Alkyl Sulfates. The Journal of Organic Chemistry, (Mar. 5, 1957) vol. 22. No. 1, pp. 86–88.

Gubanova et al., "Synthesis and Antiviral Activity of Organic and Organphosphorus Derivatives of β–aminonitriles," translated from Khimiko–farmatsevticheskii Zhurnal, 26, No. 7–8, pp. 60–62 (1992).

(List continued on next page.)

*Primary Examiner*—Joseph D. Anthony
*Attorney, Agent, or Firm*—Joel J. Hayashida

[57] ABSTRACT

The invention provides liquid cleaning or bleaching compositions containing compounds having the structure of Formula I

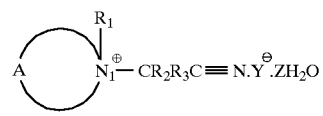

wherein A is a saturated ring formed by five atoms in addition to the $N_1$ atom, the five saturated ring atoms being four carbon atoms and a heteroatom, the substituent $R_1$ bound to the $N_1$ atom of the Formula I structure including either (a) a $C_{1-24}$ alkyl or alkoxylated alkyl where the alkoxy is $C_{2-4}$, (b) a $C_{4-24}$ cycloalkyl, (c) a $C_{7-24}$ alkaryl, (d) a repeating or nonrepeating alkoxy or alkoxylated alcohol, where the alkoxy unit is $C_{2-4}$, or (e) —$CR_2R_3CN$ where $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$, the $R_2$ and $R_3$ substituents are each H, a $C_{1-24}$ alkyl, cycloalkyl, or alkaryl, or a repeating or nonrepeating alkoxyl or alkoxylated alcohol where the alkoxy unit is $C_{2-4}$, and wherein Y is a generally anionic counterion and Z is in the range of 0 to 10. Additional, adjunct materials commonly found in liquid cleaning and bleaching compositions can be added.

11 Claims, 1 Drawing Sheet

6,010,994
Page 2

U.S. PATENT DOCUMENTS

| | | | |
|---|---|---|---|
| 2,774,758 | 12/1956 | Yanko | 544/163 |
| 2,848,450 | 8/1958 | Rudner et al. | 544/163 |
| 2,851,458 | 9/1958 | Billinghurst | 544/163 |
| 2,868,786 | 1/1959 | Siemer et al. | 144/115 |
| 3,532,735 | 10/1970 | Morgan | 558/455 |
| 3,689,470 | 9/1972 | Shachat et al. | 526/312 |
| 3,772,275 | 11/1973 | Hernestam et al. | 544/165 |
| 3,780,092 | 12/1973 | Samour et al. | 560/222 |
| 3,882,035 | 5/1975 | Loffelman et al. | 510/313 |
| 4,086,175 | 4/1978 | Kravetz et al. | 510/314 |
| 4,134,889 | 1/1979 | Distler et al. | 546/230 |
| 4,164,511 | 8/1979 | Distler et al. | 558/346 |
| 4,328,226 | 5/1982 | Witek et al. | 514/239.5 |
| 4,342,872 | 8/1982 | Grier et al. | 546/186 |
| 4,397,757 | 8/1983 | Bright et al. | 252/186.41 |
| 4,551,526 | 11/1985 | Mai et al. | 544/163 |
| 4,737,498 | 4/1988 | Banasiak et al. | 514/237.8 |
| 4,751,015 | 6/1988 | Humphreys et al. | 544/139 |
| 4,921,631 | 5/1990 | Gradwell et al. | 252/186.38 |
| 4,978,770 | 12/1990 | Aoyagi et al. | 558/455 |
| 5,106,528 | 4/1992 | Francis et al. | 252/186.23 |
| 5,236,616 | 8/1993 | Oakes et al. | 252/186.38 |
| 5,399,746 | 3/1995 | Steiger et al. | 560/251 |
| 5,405,412 | 4/1995 | Willey et al. | 8/111 |
| 5,460,747 | 10/1995 | Gosselink et al. | 252/186.38 |
| 5,591,378 | 1/1997 | Deline et al. | 252/186.38 |
| 5,739,327 | 4/1998 | Arbogast et al. | 544/163 |
| 5,741,437 | 4/1998 | Arbogast et al. | 252/186.39 |
| 5,792,218 | 8/1998 | Alvarez et al. | 8/111 |

FOREIGN PATENT DOCUMENTS

| | | |
|---|---|---|
| 912011707 | 5/1991 | European Pat. Off. . |
| 912012606 | 5/1991 | European Pat. Off. . |
| 0790244 | 2/1997 | European Pat. Off. . |
| 0 790 244 A1 | 8/1997 | European Pat. Off. . |
| 25035829 | 1/1975 | Germany . |
| 25557691 | 12/1975 | Germany . |
| 26204455 | 5/1976 | Germany . |
| 62-225871 | 9/1987 | Japan . |
| 63-167157 | 7/1988 | Japan . |
| 1230773 | 9/1989 | Japan . |
| 6136391 | 10/1992 | Japan . |
| WO 96/07650 | 3/1996 | WIPO ... C07D 295/14 |

OTHER PUBLICATIONS

Stanley et al., "Synthesis and Enzymatic Evaluation of Some N–Alkyl Branched Chain Piperidine Salts and N–Alkyl–3–(N,N–diethylcarbamoyl)piperidine Salts as Inhibitors of Acetyl– and Butyrycholinesterase," J. Medicinal Chemistry, 17, No. 1 (1974).

Lespagnol et al., "Guanidines monosubstituées à fonction ammonium quaternaire," Mèmoires Prèsentès a la Sociètè Chimique, paper presented at Congress of the International Pharmaceutical Federation, Zurich, Sep. 1959 (and translation).

LIQUID COMPOSITIONS CONTAINING N-ALKYL AMMONIUM ACETONITRILE SALTS

This application is a continuation in part of Ser. No. 08/475,292, filed Jun. 7, 1995, now U.S. Pat. No. 5,739,327 entitled "N-ALKYL AMMONIUM ACETONITRILE BLEACH ACTIVATORS," inventors Arbogast et al., of common assignment herewith.

FIELD OF THE INVENTION

The present invention generally relates to N-alkyl ammonium acetonitrile compounds in a liquid matrix, and particularly liquid compositions containing a source of active oxygen useful in applications such as bleaching and cleaning.

BACKGROUND OF THE INVENTION

Peroxy compounds are effective bleaching agents, and compositions including mono- or di-peroxyacid compounds are useful for industrial or home cleaning or laundering operations. For example, U.S. Pat. No. 3,996,152, issued Dec. 7, 1976, inventors Edwards et al., discloses bleaching compositions including peroxygen compounds such as diperazelaic acid and diperisophthalic acid.

Peroxyacids (also known as "peracids") have typically been prepared by the reaction of carboxylic acids with hydrogen peroxide in the presence of sulfuric acid. For example, U.S. Pat. No. 4,337,213, inventors Marynowski et al., issued Jun. 29, 1982, discloses a method for making diperoxyacids in which a high solids throughput may be achieved.

However, bleaching products containing peroxyacid compounds tend to lose bleaching activity during storage, due to decomposition of the peroxyacid. The relative instability of peroxyacid can present a problem of storage stability for compositions consisting of or including peroxyacids.

One approach to the problem of reduced bleaching activity of peroxyacid compositions has been to include activators of peroxyacids. U.S. Pat. No. 4,772,290, issued Sep. 20, 1988, inventors Mitchell et al., and U.S. Pat. No. 4,900,469, issued Feb. 13, 1990, inventors Farr et al., both of which are of common assignment herewith, disclose stable organic bleach activators suspended in a liquid hydrogen peroxide matrix.

U.S. Pat. No. 4,915,863, issued Apr. 10, 1990, inventors Aoyagi et al., discloses compounds said to be peracid precursors that have nitrile moieties. U.S. Pat. No. 5,236,616, issued Aug. 17, 1993, inventors Oakes et al., discloses compounds said to be cationic peroxyacid precursors that have nitrile moieties. These nitrile containing activators do not contain a leaving group, such as found in ester-type bleach activators, but instead include a quaternary ammonium group suggested as activating the nitrile and said, upon hydrolysis in the presence of hydrogen peroxide, to generate a peroxyimidic acid as bleaching species. The Aoyagi et al. activators include an aromatic ring, which tends to cause fabric yellowing.

German patent application DE OS 44 312 12, published Mar. 7, 1996, describes production of quaternized glycinonitriles in the form of stable aqueous solutions.

In the parent application, Ser. No. 08/475,292, now U.S. Pat. No. 5,739,327 N-methylmorpholinium acetonitrile methylsulfate ("MMA") is noted as being of special interest. The MMA is useful as an activator in bleaching applications when combined with a source of active oxygen. These compounds and related ones, however, may be incorporated into liquid formulations, both with and without a source of active oxygen.

SUMMARY OF THE INVENTION

The present invention provides liquid cleaning or bleaching compositions comprising compounds having the structure of Formula I

FORMULA I

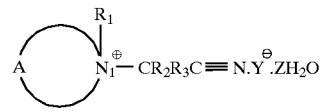

wherein A is a saturated ring formed by five atoms in addition to the $N_1$ atom, the five saturated ring atoms being four carbon atoms and a heteroatom, the substituent $R_1$ bound to the $N_1$ atom of the Formula I structure including either (a) a $C_{1-24}$ alkyl or alkoxylated alkyl where the alkoxy is $C_{2-4}$, (b) a $C_{4-24}$ cycloalkyl, (c) a $C_{7-24}$ alkaryl, (d) a repeating or nonrepeating alkoxy or alkoxylated alcohol, where the alkoxy unit is $C_{2-4}$, or (e) —$CR_2R_3C \equiv N$ where $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$, the $R_2$ and $R_3$ substituents are each H, a $C_{1-24}$ alkyl, cycloalkyl, or alkaryl, or a repeating or nonrepeating alkoxyl or alkoxylated alcohol where the alkoxy unit is $C_{2-4}$, and wherein Y is a generally anionic counterion and Z is in the range of 0 to 10.

The Formula I compounds have a quaternary nitrogen atom ($N_1$), requiring the presence of at least one counterion (Y) to be associated therewith. Counterions for the inventive salts include both organic and inorganic anions, preferably alkylsulfate, especially methylsulfate, sulfate or bisulfate, tosylate and mesylate, and chloride, bromide, and nitrate. Especially preferred are methylsulfate, sulfate, bisulfate, tosylate and mixtures thereof, which have been found to result in surprisingly advantageous properties for the novel Formula I compounds. Additionally, although Y has been indicated in Formula I to be monovalent, in fact, it can be multivalent. As an example, when Y is sulfate, the counterion is divalent. Accordingly, these inventive salts are particularly well suited to bleaching and cleaning compositions.

The novel compounds with the Formula I structure are particularly useful when formulated as compositions that include a source of active oxygen, and these compositions provide excellent bleaching in alkaline solutions.

Preferred embodiments of the invention include lower alkyls substituted at the $N_1$, e.g. N-methyl morpholinium acetonitrile, N-ethyl morpholinium acetonitrile, N-butyl morpholinium acetonitrile, which are illustrated by Formula II (with "n" preferably being 0 to 24 and where "Y" is one of the above described counterions).

FORMULA II

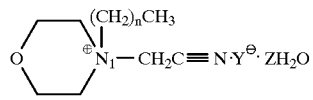

A particularly preferred embodiment of the invention are liquid compositions containing N-methyl morpholinium acetonitrile methylsulfate, sulfate, bisulfate salts (sometimes designated as, respectively, "MMAMS," "MMAS" or "MMABS," where "n" of Formula II is 0), or mixtures thereof, which have excellent stability, and which show excellent bleaching and cleaning performance when formulated with a source of active oxygen in alkaline wash water. Tosylate salts are also preferred and would be designated as "MMATS."

When formulated with a source of active oxygen, compositions of the invention are useful as or in home cleaning and laundry products, such as bleaching additives, detergents, detergent boosters, detergents with bleach, bleaches, bleaching aids, dishwashing detergents, surface and mildew stain removers, and spot treatment products such as stain removers, prewash and presoak laundry aids. Among the advantages derived from compositions of the invention are improved cleaning, stain removal, spot removal, whitening, and brightening of treated articles.

DETAILED DESCRIPTION OF THE PREFERRED EMBODIMENTS

Figure 1:
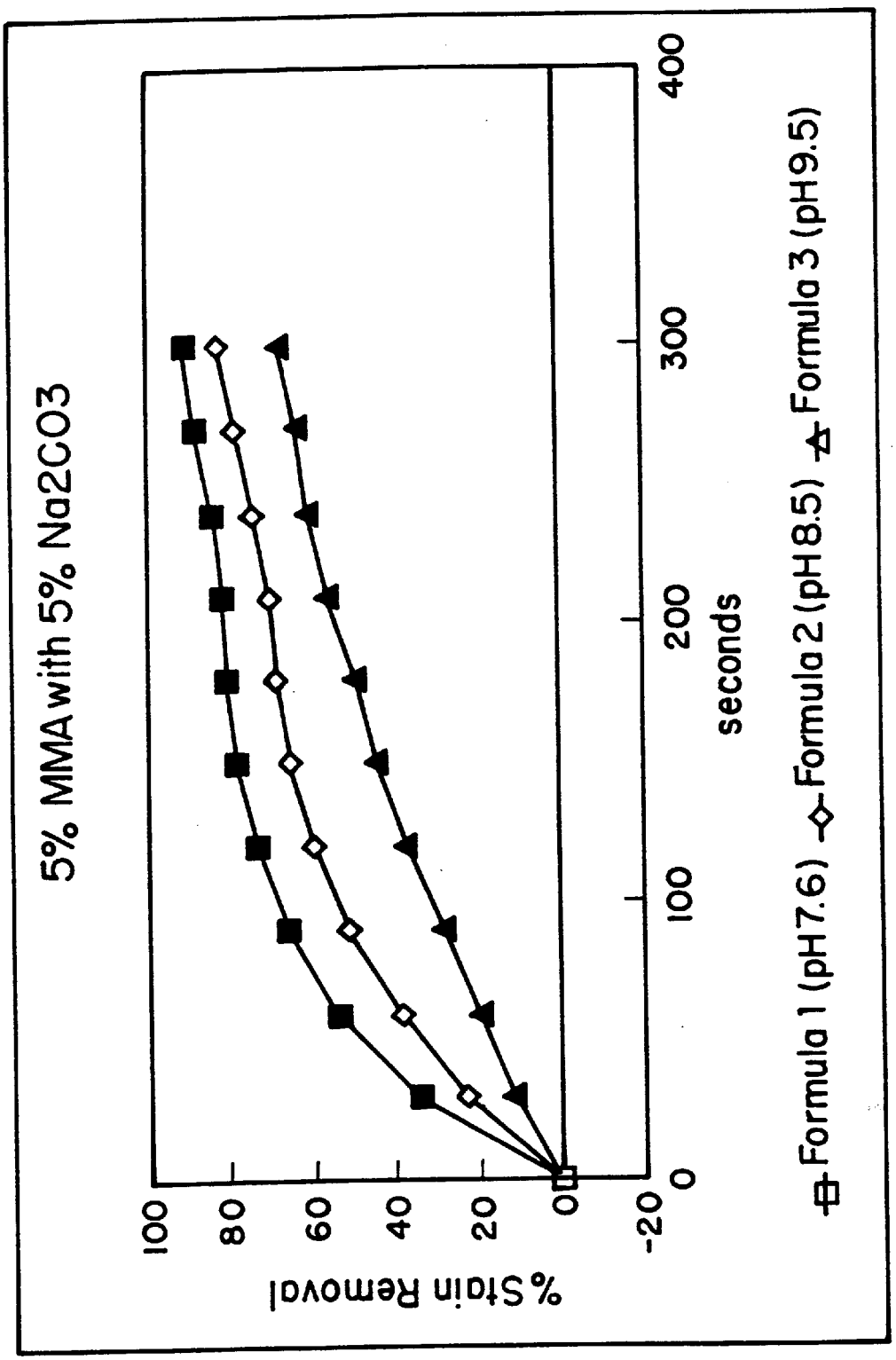
FIG. 1 shows a graph depicting performance of a preferred embodiment of the invention formulated as a hard surface cleaner at various pH's.

The novel compounds used in the invention include certain nitrites having the structure illustrated by Formula I. The $N_1$ atom of the Formula I compound is part of a saturated ring, illustrated by "A" in Formula I.

FORMULA I

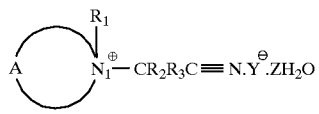

This saturated ring of which $N_1$ is a part has five atoms in addition to $N_1$, with at least one heteroatom being in the saturated ring in addition to the $N_1$, preferably wherein the heteroatom of the ring is an oxygen atom or a sulfur atom.

The $N_1$ atom shown in Formula I is N-acetonitrile substituted and also quaternized. Without being bound by theory, it is believed that the electron withdrawing nature of the quaternary nitrogen may be increased by being part of a saturated, heterocyclic ring and may also function to improve the hydrophilic character of the oxidant.

A substituent $R_1$ will be bonded to the $N_1$ atom of the Formula I structure and additionally a nitrile moiety (—$CR_2R_3C\equiv N$) is bonded to the $N_1$ atom, where $R_2$ and $R_3$ are each H, a $C_{1-24}$ alkyl, cycloalkyl, or alkylaryl, or a repeating or nonrepeating alkoxyl or alkoxylated alcohol where the alkoxy unit is $C_{2-4}$. The $R_1$ substituent may be a $C_{1-24}$ alkyl or alkoxylated alkyl where the alkoxy is $C_{2-4}$, a $C_{4-24}$ cycloalkyl, a $C_{7-24}$ alkylaryl, a repeating or nonrepeating alkoxy or alkoxylated alcohol, where the alkoxy unit is $C_{2-4}$, and illustrative such groups are, for example,

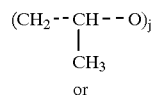

or

-continued

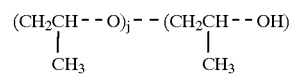

where j=1 to 24. The $R_1$ substituent may also be another —$CR_2R_3C\equiv N$, and again $R_2$ and $R_3$ are each H, a $C_{1-24}$ alkyl, cycloalkyl, or alkylaryl, or a repeating or nonrepeating alkoxyl or alkoxylated alcohol where the alkoxy unit is $C_{2-4}$, and illustrative such groups are:

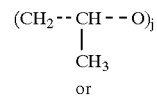

or

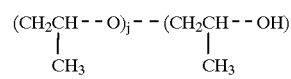

where j=1 to 24.

Particularly preferred activator embodiments are illustrated by Formula II (where "Y" is as earlier described and "n" is 0 to 24.

FORMULA II

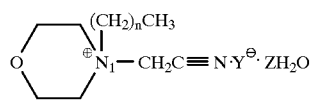

Novel derivatives used in the liquid compositions of the invention include peroxyimidic intermediates that are believed formed from the novel nitrites in the presence of an active oxygen source. So formed, peroxyimidic derivatives typically would be short-lived intermediates formed in situ when the nitrites of the invention interact with a source of hydrogen peroxide and where the reactive nitrile moiety forms a peroxyimidic acid. However, such peroxyimidic derivatives may also be prepared in situ by analogy to syntheses known in the art.

1. Counterions

Since compounds of the invention are typically quaternized, they will include at least one counterion (designated as "Y"), selected from a wide variety of anionic counterions, especially alkylsulfate (e.g., methylsulfate), sulfate or bisulfate, or mixtures thereof, mesylate and tosylate. In the copending parent application of which this is a continuation-in-part, N-alkyl ammonium acetonitrile compounds are disclosed as typically including such wide variety of counterions such as chloride, bromide, nitrate, alkyl sulfate, and the like. There, the preferred embodiment was described as N-methyl ammonium acetonitrile methyl sulfate. In addition, in the present invention of sulfate or bisulfate salt may be produced from heated and acidified MMA (as methyl sulfate). However, the sulfate and bisulfate salts appear to exist in an equilibrium, the predominance of one over the other dependent upon pH. Three preferred salts are illustrated by Formulas IIIA, IIIB and IIIC.

FORMULA III

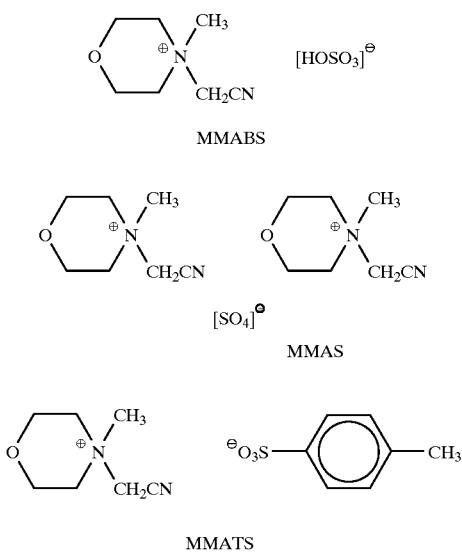

2. Bleaching and Cleaning Compositions

Bleaching and cleaning compositions of the invention include the Formula I nitrile salts as activator, together with a source of active oxygen.

The peroxide or active oxygen source for compositions of the invention may be selected from most preferably hydrogen peroxide, Caro's acid (peroxymonosulfuric acid), and then, as suspended particulate oxidants, the alkali metal and alkaline metal salts of percarbonate, perborate, persilicate and hydrogen peroxide adducts. Examples of hydrogen peroxide formulations suitable for use herein include those depicted in Mitchell et al., U.S. Pat. No. 4,900,468, Farr et al., U.S. Pat. No. 5,180,514 and Baker et al., U.S. Pat. No. 4,764,302, all of common assignment and all of which are incorporated herein by reference. Where sodium percarbonate, sodium perborate mono- and tetrahydrate, are utilized in aqueous formulations, it is most preferable to suspend them in such aqueous formulations, along with stabilizers. Exemplary of these systems are Peterson et al., U.S. Pat. No. 5,464,552, Published European Patent Applications EP 294 904 and EP 293 040, incorporated herein by reference. Other peroxygen sources may be possible, such as monopersulfates and monoperphosphates, or their equivalent aqueous forms, such as monopersulfuric acid, known in the trade as Caro's acid or Caroate®, a product of BASF AG, Germany; and poorly soluble oxidants, such as alkaline earth peroxides, for example, Gray et al., U.S. Pat. Nos. 4,891,147 and 5,019,189, both of which are incorporated herein by reference. Alternatively, the formulations of the invention may be essentially nonaqueous. These nonaqueous formulations will have a nonaqueous liquid as the continuous phase, such as nonionic surfactant, or nonaqueous organic solvents such as glycol ethers, hydrocarbons, acids, alcohols, and the like. A nonaqueous formulation would be expected to be highly chemically stable because bleach activators such as MMA are less likely to be hydrolyzed in the nonaqueous continuous matrix. Exemplary nonaqueous formulations are depicted in Peterson et al., U.S. Pat. No. 4,874,537, and Van Buskirk et al., U.S. Pat. No. 5,415,796, both of which are incorporated herein by reference.

The range of peroxide to activator is preferably determined as a molar ratio of peroxide to activator. Thus, the range of peroxide to each activator is a molar ratio of from about 0.1:1 to 100:1, more preferably about 1:1 to 10:1 and most preferably about 2:1 to 8:1. This peracid activator/peroxide composition should provide about 0.5 to 100 ppm A.O., more preferably about 1 to 50 ppm peracid A.O. (active oxygen), and most preferably about 1 to 20 ppm peracid A.O., in aqueous media for typical laundry applications. Formulations intended for hard surface cleaning will more typically have peracid activator/peroxide providing from about 0.5 to 500,000 ppm A.O., more preferably about 1 to 20,000 ppm peracid A.O., and most preferably about 1 to 10,000 ppm peracid A.O.

However, one of the advantages of the inventive MMA compounds is that those tested have been found to be oxidatively stable when formulated with hydrogen peroxide, preferably at a low pH. This allows for great flexibility when formulating liquid products since the MMA compounds do not necessarily need to be kept separate from the source of active oxygen.

Compositions of the invention have been found to provide superior bleaching (cleaning and stain removal) benefits on common laundry and household stains.

3. Delivery Systems

The liquid compositions of the invention can take numerous desirable forms. For example, without limitation, these include macroemulsions, microemulsions, structured liquids, liquid crystals, vesicular systems, lamellar systems, suspensions, dispersions, gels, mulls and pastes. These liquid systems can be clear or translucent (such as microemulsions) to opaque. These liquid systems can either be cleaning liquids wherein the inventive compounds are present as potentially antimicrobial actives, or, where a source of peroxygen (active oxygen) is present, as a bleaching liquid, as well as detergents and detergent bleaches. They can also be either unitary systems, or multiple deliveries, such as, for example, a dual chamber container, one chamber containing the inventive N-alkyl ammonium acetonitrile compounds with a source of active oxygen, while the other contains a solution including actives sensitive to oxidation, for example, enzymes and fluorescent whitening agents. An example of a container which can co-dispense these two different liquid compositions is found in Beacham et al., U.S. Pat. No. 4,585,150, incorporated herein by reference; and an example of a system where a dual delivery is depicted, with one part containing a liquid oxidant formulation, the other, a liquid with materials which are sensitive to oxidation, is found in Co-pending applications of Choy et al., Ser. Nos. 08/605,822 now U.S. Pat. No. 5,767,005, and 08/605,824, both filed Feb. 23, 1996, and both entitled "Composition and Apparatus for Surface Cleaning," of common assignment, incorporated herein by reference. In the case of more viscous forms, such as gels, mulls or pastes, the continuous phase can be nonionic surfactants, and is exemplified by Kaufmann et al., U.S. Pat. Nos. 4,743,394 and 5,362,413, both of which are incorporated herein by reference.

The liquid compositions of this invention frequently contain varying amounts of surfactants, which may act both as a cleaning active ingredient, but also to help disperse sparingly soluble materials in the liquid phase, or which may serve as the continuous phase in an essentially nonaqueous composition.

4. Surfactants

Surfactants with which the activators and active oxygen compositions may be combined or admixed include linear ethoxylated alcohols, such as those sold by Shell Chemical Company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof. Shell Chemical, Huntsman Chemical and Union Carbide are among the numerous producers of these surfactants.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers or propylene oxide and ethylene oxide with propoxylated ethylene diamine. Also included are such semi-polar nonionic surfactants like amine oxides (such as Ammonyx from Stepan and Barlox from Lonza), phosphine oxides, sulfoxides and their ethoxylated derivatives.

Anionic surfactants may also be suitable. Examples of such anionic surfactants may include the ammonium, substituted ammonium (e.g., mono-di-, and triethanolammonium), alkali metal and alkaline earth metal salts of $C_6$–$C_{20}$ fatty acids and rosin acids, linear and branched alkyl benzene sulfonates, alkyl sulfates, alkyl ether sulfates, alkane sulfonates, alpha olefin sulfonates, hydroxyalkane sulfonates, fatty acid monoglyceride sulfates, alkyl glyceryl ether sulfates, acyl sarcosinates and acyl N-methyltaurides.

Suitable cationic surfactants may include the quaternary ammonium compounds in which typically one of the groups linked to the nitrogen atom is a $C_{12}$–$C_{18}$ alkyl group and the other three groups are short chained alkyl groups which may bear inert substituents such as phenyl groups.

Suitable amphoteric and zwitterionic surfactants containing an anionic water-solubilizing group, a cationic group or a hydrophobic organic group include amino carboxylic acids and their salts, amino dicarboxylic acids and their salts, alkyl-betaines, alkyl aminopropylbetaines, sulfobetaines, alkyl imidazolinium derivatives, certain quaternary ammonium compounds, certain quaternary phosphonium compounds and certain tertiary sulfonium compounds.

These and other types of surfactants are exemplified in *McCutcheon's Emulsifiers and Detergents* (1994) and *Kirk-Othmer Encyclopedia of Chemical Technology 3rd*, Vol. 22, "Surfactants," pp. 332–432 (1983), both of which are incorporated herein by reference.

Other common detergent adjuncts may be added if a bleach or detergent bleach product is desired; See 6 below.

5. Source of Acid/Alkali

Compositions of the invention, when combined with a source of active oxygen, preferably function for bleaching best at a neutral to alkaline pH, but are shelf stabilized best at an acidic pH. Thus, compositions of the invention preferably include a source of protons as an "acid sink." This can be achieved by having a mineral or organic acid present. These include, but are not limited to, mineral acids selected from phosphoric, sulfuric, hydrochloric, nitric, carbonic, boric, sulfamic, sulfurous acids and mixtures thereof; and organic acids selected from acetic, hydroxyacetic (glycolic), citric, succinic, maleic benzoic, oxalic acids, and mixtures thereof. It may also be possible to use the acidic forms of materials ordinarily viewed as hydrotropes, such as toluene sulfonic acid, xylene sulfonic acid, cumene sulfonic acid, and the like; and surfactants, such as alkylbenzene sulfonic acid (also known as HLAS), exemplary of which is dodecyl benzene sulfonic acid (See Choy et al., U.S. Pat. Nos. 4,759,867, 4,804,491 and 4,895,669, incorporated herein by reference). However, the compositions of the invention can also be pH adjusted for a variety of applications, such as when used as a mildew or other type of stain remover.

When the composition is ready for use as a laundry additive, it is especially advantageous to have an amount of alkaline buffer present sufficient to maintain a pH greater than about 6.0, more preferably in the range of about 8.5 to about 10.5 for most effective bleaching, when the liquid formulation is dispensed into an aqueous wash system. As a hard surface cleaner, on the other hand, it may be useful to co-dispense the alkaline buffer in a separate, preferably liquid, composition. These alkaline buffers include, but are not limited to, alkali metal hydroxides (sodium, lithium, potassium), ammonium hydroxide, alkali metal ortho-, meta- and pyrophosphates, alkali metal silicates, alkali metal tetraborates (penta- and decahydrates), alkali metal and ammonium carbonates, alkali metal and ammonium carbamates (See Garabedian, Jr., et al., U.S. Pat. Nos. 5,523,024, 5,468,423, 5,437,807 and 5,252,245, all incorporated herein by reference), alkali metal and ammonium polyacrylates, alkali metal and ammonium succinates, alkali metal and ammonium maleates and additional conjugate bases of weak organic acids, such as those mentioned hereinabove. Further, organic bases are included, such as, without limitation, ethanolamine, diethanolamine, triethanolamine, hydroxyamine, methylamine, dimethylamine and trimethylamine. On the other hand, acidic hard surface cleaners are certainly well known and preferred for use as bathroom cleaners. These types of cleaners therefore are acidified with the type of acids described hereinabove.

6. Additional Functional/Aesthetic Adjuncts

Other adjuncts (useful in cleaning and laundering applications) are optionally included in the inventive compositions. Dyes include anthraquinone and similar blue dyes. Pigments may also be used. Monastral colorants are also possible for inclusion. Brighteners or whiteners, such as stilbene, styrene and styrylnaphthalene brighteners (fluorescent whitening agents), may be included. Fragrances used for aesthetic purposes are commercially available from Quest, Sozio, Firmenich, Dragoco, Bush Broke and Allen, Norda, International Flavors and Fragrances and Givaudon. Stabilizers include hydrated salts, such as magnesium sulfate, and boric acid.

In some of the compositions herein, adjuvants include (and are especially preferred) a chelating agent or sequestrant, most preferably, an aminopolyphosphonate. These chelating agents assist in maintaining the solution stability of the salt activators and active oxygen source in order to achieve optimum performance. In this manner, they are acting to chelate heavy metal ions, which cause catalyzed decomposition of the (believed) in situ formed peroxyimidic acids, although this is a non-binding theory of their action and not limiting.

The chelating agent is selected from a number of known agents which are effective at chelating heavy metal ions. The chelating agent should be resistant to hydrolysis and rapid oxidation by oxidants. Preferably, it should have an acid dissociation constant (pKa) of about 1–9, indicating that it dissociates at low pH's to enhance binding to metal cations. Acceptable amounts of the (optional) chelating agent range from 0–1,000, more preferably 5–500, most preferably 10–100 ppm chelating agent, in the wash liquor. As a hard surface cleaner, however, it is preferred to add amounts of the chelating agent form 0–100,000, more preferably 5–50,000, and most preferably 10–10,000 ppm chelating agent.

The most preferred chelating agent is an aminopolyphosphonate, which is commercially available under the trademark Dequest from Monsanto Company. Examples thereof are Dequest 2000, 2041 and 2060. (See also Bossu U.S. Pat. No. 4,473,507, column 12, line 63 through column 13, line 22, incorporated herein by reference.) A polyphosphonate, such as Dequest 2010, is also suitable for use.

Other chelating agents, such as ethylenediaminetetraacetic acid (EDTA) and nitrilotriacetic acid (NTA) may also be suitable for use. Still other new, preferred chelating agents are new propylenediaminetetraacetates, such as Hampshire 1,3 PDTA, from W.R. Grace, and Chel DTPA 100#F, from Ciba Geigy A.G. Mixtures of the foregoing may be suitable.

Additional desirable adjuncts are enzymes (although it may be preferred to also include an enzyme stabilizer). Proteases are one especially preferred class of enzymes. They are preferably selected from alkaline proteases. The term "alkaline," refers to the pH at which the enzymes' activity is optimal. Alkaline proteases are available from a wide variety of sources, and are typically produced from various microorganism (e.g., *Bacillus subtilisis*). Typical examples of alkaline proteases include Maxatase and Maxacal from International BioSynthetics, Alcalase, Savinase, and Esperase, all available from Novo Nordisk A/S. See also Stanislowski et al., U.S. Pat. No. 4,511,490, incorporated herein by reference. Further suitable enzymes are amylases, which are carbohydrate-hydrolyzing enzymes. It is also preferred to include mixtures of amylases and proteases. Suitable amylases include Rapidase, from Société Rapidase, Milezyme from Miles Laboratory, and Maxamyl from International BioSynthetics.

Still other suitable enzymes are cellulases, such as those described in Tai, U.S. Pat. No. 4,479,881, Murata et al., U.S. Pat. No. 4,443,355, Barbesgaard et al., U.S. Pat. No. 4,435,307, and Ohya et al., U.S. Pat. No. 3,983,082, incorporated herein by reference.

Yet other suitable enzymes are lipases, such as those described in Silver, U.S. Pat. No. 3,950,277, Thom et al., U.S. Pat. No. 4,707,291, and Wiersema et al., U.S. Pat. Nos. 5,296,161 and 5,030,240, and Poulose et al., U.S. Pat. No. 5,108,457, incorporated herein by reference.

The hydrolytic enzyme should be present in an amount of about 0.01–5%, more preferably about 0.01–3%, and most preferably about 0.1–2% by weight of the detergent. Mixtures of any of the foregoing hydrolases are desirable, especially protease/amylase blends.

Some of the adjuncts, such as fluorescent whitening agents, enzymes and pigments, are sensitive to oxidants, and thus, may need to be co-dispensed in a separate liquid formulation. On the other hand, there are encapsulation methods and other protective additives available for these sensitive materials, such as, for example, from Coyne et al., U.S. Pat. Nos. 4,863,626, 5,093,021, and 5,225,102 and DeLeeuw et al., U.S. Pat. Nos. 5,254,287 and 5,167,854, incorporated herein by reference.

In some of the embodiments of this invention, such as when the delivery execution is a multiple delivery of liquid formulations, there may be a need for a viscosity/phase modifier. Exemplary such materials include alkanolamines, especially triethanolamine, and a wide variety of polymers, including water soluble to water-miscible polymers, such as polyethylene gycol, polyvinyl alcohol, polyvinyl acetate, polyacrylic acid, co-polymers of acrylic acid, co-polymers of methacrylic acid, and the salts thereof. Other polymers include starch, xanthan gum, gum arabic and other naturally occurring polymers. Nonaqueous systems, on the other hand, can be thickened with silicas, such as xerogels and fumed and precipitated silicas, such as Cab-O-Sil.

Anti-redeposition agents, such as carboxy methylcellulose, are potentially desirable. Foam boosters, such as appropriate anionic surfactants, may be appropriate for inclusion herein. Also, in the case of excess foaming resulting from the use of certain surfactants, anti-foaming agents, such as alkylated polysiloxanes, e.g. dimethylpolysiloxane, would be desirable.

In certain hard surface cleaners, it is desirable to incorporate a source of particulate matter to act as abrasives. Abrasives are desirable adjuncts for cleaning especially persistent stains. Abrasives can be selected from a wide variety of particulate materials, including, but not limited to, calcium carbonate, glass beads, polymer beads, perlite, silica sand and various other insoluble, inorganic particulate abrasives are also possible, such as quartz, pumice, feldspar, tripoli and calcium phosphate. See Brodbeck et al., U.S. Pat. No. 5,529,711, and Choy et al., U.S. Pat. Nos. 5,554,321 and 5,470,499, all of which are incorporated herein by reference. Other types of abrasives include water soluble materials present in an amount such as to exceed their solubility in water, leaving a portion thereof undissolved. These types of materials include alkali metal bicarbonates, alkali metal phosphates, alkali metal borates, particularly sodium tetraborate decahydrate (borax) and pentahydrate (see U.S. patent application Ser. No. 08/718,059, filed Sep. 17, 1996, entitled "Cleaner with Water Soluble Abrasive," incorporated herein by reference.).

7. Liquid Medium

So that the correct amount of active ingredients are dosed, the inventive compounds are combined with a liquid medium, most preferably, an inert, nonreactive liquid. Generally speaking, this nonreactive liquid is principally water, or water combined with solvents, or nonaqueous solvents. For bench scale experiments, it is preferred to use deionized water, although in the large scale manufacture of the inventive liquid compositions, this may not be necessary. The solvents can be chosen from any organic or inorganic solvents. Some preferred organic solvents are those with a vapor pressure of at least 0.001 mm Hg at 25° C. and soluble to the extent of at least 1 g/100 ml water. The organic solvents used in the invention are preferably selected from $C_{1-6}$ alkanol, $C_{3-24}$ alkylene glycol ether, and mixtures thereof. However, other, less water soluble or dispersible organic solvents may also be utilized. The alkanol can be selected from methanol, ethanol, n-propanol, isopropanol, butanol, pentanol, hexanol, their various positional isomers, and mixtures of the foregoing. It may also be possible to utilize in addition to, or in place of, said alkanols, the diols such as methylene, ethylene, propylene and butylene glycols, and mixtures thereof. Other solvents, such as amines, ketones, ethers, esters, carboxylic acids, oils, hydrocarbons and halides may be used alone, or mixtures thereof In the case of certain amines, e.g., monoethanolamine, diethanolamine, etc., such solvents are also considered buffers (as described further above in 6). Thus, it is possible that, in certain instances, these amines can be bifunctional herein. Other examples of solvents can be found in *Kirk-Othmer, Encyclopedia of Chemical Technology* 3rd, Vol. 21, pp. 377–401 (1983), incorporated by reference herein. Where the formulation is a nonaqueous one, liquid nonionic surfactants, as previously mentioned, can be used to provide the continuous phase. Additionally, an inorganic or organic acid, such as listed above in 5, could be used as the continuous phase.

8. Applications a. Laundry Products

Compositions of the invention are useful as or in laundry products, such as bleaching additives, detergents, detergent boosters, detergents with bleach, bleaches, bleaching aids, and stain removers. Among the advantages derived from compositions of the invention are improved cleaning, stain removal, spot removal, whitening, and brightening of treated articles.

Further benefits from use of the inventive compositions include scavenging of free dye during laundering to prevent dye transfer between garments (sometimes known as dye transfer inhibition).

b. Surface Cleaners

Other product applications include household cleaning products, such as hard surface cleaners to be dissolved in water prior to use. Exemplary surface cleaners are tile and grout cleaners, bathroom (floor, toilet, and counter) and kitchen (floor, sink, and counter) cleaners. Additionally, kitchen products such as dishwasher detergents with bleach or bleach cleaning and scrubbing pads are contemplated. Among the benefits derived from use of the inventive compositions in such applications are improved stain and spot removal and general cleaning of the treated surfaces to remove food, rust, grime, mildew, mold, and other typical stains found on such surfaces.

In the hard surface cleaning area, the present invention has been found to benefit from more acidic conditions (i.e., lower pH's) than for laundry formulations. These pH's can be from about 0 to about 8, more preferably between about 2 and 7.5 At these lower pH levels, the extent of bleaching—when the hard surface cleaner is formulated with both the MMA compound and a source of active oxygen—appears to become improved.

In one preferred embodiment of a hard surface cleaner delivery, as in the laundry product formulation, a dual chambered container/dispenser is preferred. One chamber contained an $H_2O_2$/MMA solution at an acidic pH. The other chamber contained agents to adjust the pH to the optimum level, namely, an alkaline buffer and optionally, a surfactant. Other agents could be included for improved cleaning performance (thickeners, chelating agents, builders, etc.) or aesthetic appeal (dyes, colorants, fragrances). The preferred delivery is a trigger sprayer, which must blend the two solutions/fluids from the two chambers prior to delivering the combined solutions as a spray. This could be accomplished by either a mixing chamber, or by directing two fluid streams to a common target point by means of a diverter or other redirection means. The surfactant or surfactants used in the other chamber could be selected from the diverse variety disclosed above in 4. Further, it is common to include in hard surface cleaners at least one solvent to further enhance cleaning performance and to disperse hydrophobic or poorly soluble materials into the liquid cleaner. Fragrances and colorants as provided from 6 are also desirable. Buffers selected from the various acids/alkaline materials disclosed from 5 are desirable, as well as thickening agents which allow the blended liquids to cling to vertical surfaces, such as colloids (clays, alumina, silica) or surfactants, surfactant/solvent mixtures, or polymers. The thickening effect may be created in situ as the two liquid streams are blended at the nozzle or other delivery orifice, or pre-exist in thickened form. The molar ratio of active oxygen:MMA differs from its concentration in laundry product formulations in that a higher total amount is often present. For example, the molar ratio can range from about 100:1 to about 1:10, more preferably about 10:1 to about 1:1, most preferably about 5:1 to about 1:1 $H_2O_2$:MMA.

Additionally, non-household product applications are contemplated where an effective level of active oxygen generated in situ to treat water is useful. Illustrative of such applications are pool and spa additives, as well as cleaners to remove stains on outdoor concrete, stucco, siding, wood and plastic surfaces.

The advantages of a liquid cleaning or laundry product are quite evident. First, the MMA compounds are stable in hydrogen peroxide, allowing versatility in formulation. A single container or dual or multiple container delivery can be formulated. Liquid cleaning and laundering products appear to be greatly desired by consumers and it is advisable for the product formulator to offer liquid products as an alternative or preferred consumer product. In laundry products, the liquid product is desirable to prespot or target stains on soiled fabrics and garments.

Aspects of the invention will now be illustrated by the following examples. It will be understood that these examples are intended to illustrate, and not to limit, the invention.

EXPERIMENTAL

Example 1

In general, N-quaternary acetonitrile compounds are readily prepared from N-acetonitrile precursors by employing selected alkyl halides and using well-known synthetic approaches, such as are described by Menschutkir, *Z. Physik Chem.*, 5, 589 (1890), and *Z. Physik. Chem.*, 6, 41 (1890); Abraham, *Progr. Phys. Org. Chem.*, 11, 1 (1974); and Arnett, *J. Am. Chem. Soc.*, 102, 5892 (1980). Further methods are depicted in German patent application DE OS 44 312 12, published Mar. 7, 1996, and in the concurrently filed and application Ser. No. 08/905,511, filed Aug. 4, 1997, a continuation of then concurrently filed and application Ser. No. 08/758,542, now abandoned, of inventors Ulrich Annen et al., entitled "Process for Preparing N-Alkyl Ammonium Acetonitrile Compounds" (JSS Docket No.: 0409.073US5') both of which are incorporated herein by reference.

Compounds having the Formula I structure have a saturated ring formed by a plurality of atoms, broadly ranging from 3 to 9, although preferably containing 6 atoms including the $N_1$ atom. Preparation of these compounds will most conveniently start with a compound already having the formed ring. For example, a number of preparations of inventive nitrites hereinafter described will begin with a morpholine (see, e.g., the Formula II structure). An example of three membered rings is aziridine, e.g., N-methylacetonitrile aziridinium; as an example of four membered rings there is azetidine, e.g., N-ethyl-N-methylacetonitrile azetidinium; as an example of five membered rings there is pyrrolidine, e.g., N-butylacetonitrile pyrrolidinium; as an example of six membered rings, in addition to morpholine, there is piperidine, e.g., acetonitrile piperidinium; as an example of seven membered rings there is homopiperidinium; as an example of eight membered rings there is tropane, e.g., N-methylacetonitrile-8-azabicyclo[3.2.1]octane; and, as an example of nine membered rings there is octahydroindole, e.g., N-methylacetonitrile octahydroindolinium.

More particularly, in the preferred method of preparation a suitable amine is reacted with a monoaldehyde or a dialdehyde in an aqueous medium (Step A) followed by subsequent quaternization (Step B) with an alkylating agent. In Step A, the reaction is preferably either in the pH range from 8 through 14, or the pH value is maintained at not less than 2 in Step B.

Thus, an amine with the formula

is reacted as Step A with a monoaldehyde or a dialdehyde $R^6$-CHO or OHC-$R^5$-CHO, whereby $R^5$ is a chemical bond or a $C_1$ to $C_6$ alkylene bridge, or an oxyalkylene bridge, and $R^6$ stands for H or $C_{1-20}$ alkyl, and with hydrogen cyanide or an alkali metal cyanide in an aqueous medium. Step B is quaternization with an alkylating agent $R^1$-X in an aqueous medium without isolating the intermediate product from Step A.

In Step A, cyanohydrins, e.g., formadehyde cyanohydrin, can be formed as by-products from the aldehyde, that is used, and hydrogen cyanide. These cyanohydrins do not react further with the alkylating agent in Step B so that renewed breaking down of the cyanohydrins into aldehyde and hydrogen cyanide in the final product is possible.

Without the procedure in accordance with the invention, Step B usually proceeds in a such a way that, as a result of hydrolysis of the added alkylating agent the pH value of the reaction mixture drifts off from the alkaline or neutral region into the strongly acidic region with increasing reaction time. The protonation of the amine nitrogen atom of the glycinonitrile, that has not yet been quaternized, sets in—in competition with the alkylation—starting from a certain pH value so that, at the end of the addition of the alkylating agent, no further reaction of the glycinonitrile takes place. Non-quaternized glycinonitrile in the final product can also represent an undesired source of hydrogen cyanide.

Step A generates especially good results if a pH range of 9 through 13 or, especially, 10 through 12, is utilized. In this pH range, the cyanohydrin that is formed is present in an equilibrium with the aldehyde and the hydrogen cyanide so that the re-formed adducts can react to completion with the amine to give glycinonitrile.

If one also uses an excess of amine that amounts to 2 through 20 mole % or, especially about 3 through 10 mole % or, most particularly of all, about 4 through 7 mole %, based on the quantity of the hydrogen cyanide or alkali metal cyanide that is used, then one achieves even more extensive suppression of hydrogen cyanide and ancillary components, that liberate hydrogen cyanide, in the final product.

Step B generates especially good results if the pH values are not reduced below 2.5 and, especially, not below 3. An optimum pH range for the quaternization of Step B is 2.5 through 5 or, especially, 3 through 4.

Use is also made of an excess of alkylating agent that amounts to 10 to 40 mole % or, especially, 15 to 25 mole % based on the quantity of amine that is used in Step A, then one achieves still more extensive suppression of the hydrogen cyanide and the subsidiary components, that liberate hydrogen cyanide, in the final product.

Once the nitrites are prepared in quaternized form, formation of the preferred bisulfate or sulfate form preferably is by heating an alkyl sulfate form, in an acid aqueous solution. For example, a suitable elevated temperature is about 40° C. to about 1 50° C.; more preferably about 70° C. to about 110° C. The acid aqueous solution may have a pH in the range of about −1 to 6, more preferably from 0 to 3, with the heating being for a period of about 1 to 50 hours.

Aspects of the invention will now be illustrated by the following examples. It will be understood that these examples are intended to illustrate, and not to limit, the invention.

Example 2
Concentrated Laundry Additive Formulations

TABLE I discloses preferred, more preferred and most preferred ranges for a concentrated laundry additive which would be within the scope of this invention:

TABLE I

| Ingredient | Preferred Range | More Preferred Range | Most Preferred |
|---|---|---|---|
| Anionic Surfactant | 0–20% | 0–10% | 10.0% |
| Nonionic Surfactant | 0–20% | 0–10% | 8.0% |
| Nonionic Ethoxylated Surfactant | 0–20% | 0–10% | 6.5% |
| Amphoteric Surfactant | 0–20% | 0–10% | 1.5% |
| Hydrogen peroxide | 1–10% | 3–6% | 6% |
| MMA Compound[1] | 0.1–10% | 1–8% | 2% |
| Fluorescent Whitening Agent | 0–2% | 0–1% | 0.5% |
| Builder | 0–10% | 0–5% | 1% |
| Preservative | 0–0.1% | 0–0.1% | 0.02% |
| Chelating Agent | 0–5% | 0–2% | 2% |
| pH Adjusting Salt[2] | 0–5% | 0–2% | 1% |
| Viscosity Modifier | 0–10% | 0.1–5% | 3% |
| Dye/Colorant | 0–0.5% | 0–0.5% | 0–0.5% |
| Fragrance | 0–0.5% | 0–0.5% | 0–0.5% |
| Water | 0–95% | q.s. to 100% | q.s. to 100% |

[1]Inventive compound, preferably MMAMS, MMAS, MMABS or MMATS.
[2]Can be either acid or alkali, depending on pH of formulation resulting from other ingredients. In general, it is desirable to attain, for optimal chemical storage stability, a final product pH from −1–5, more preferably 0–2 and most preferably 0–1. The acids and bases described in 5. above are utilized.

In the remaining examples, the same footnotes apply and will not be repeated.

In the next Example, a dual delivery system as discussed in 3, above, is disclosed which would be within the invention.

Example 3
Two Part Concentrated Laundry Additive (Dual Chamber Bottle)

| Ingredient | Preferred Range | More Preferred Range | Most Preferred |
|---|---|---|---|
| Part A (1st Chamber) | | | |
| Anionic Surfactant | 0–30% | 0–20% | 10.0% |
| Nonionic Surfactant | 0–30% | 0–20% | 10.0% |
| Hydrogen Peroxide | 1–10% | 3–6% | 6% |
| MMA | 0.1–10% | 1–8% | 2% |
| Preservative | 0–0.1% | 0–0.1% | 0.02% |
| Chelating Agent | 0–5% | 0–2% | 2% |

-continued

| Ingredient | Preferred Range | More Preferred Range | Most Preferred |
|---|---|---|---|
| pH Adjusting Salt | 0–5% | 0–2% | 1% |
| Dye/Colorant | 0–0.5% | 0–0.5% | 0–0.5% |
| Water | 0–95% | q.s. to 100% | q.s. to 100% |
| Part B (2nd Chamber) | | | |
| Nonionic Ethoxylated Surfactant | 0–30% | 0–20% | 6.5% |
| Amphoteric Surfactant | 0–30% | 0–20% | 1.5% |
| Enzymes | 0–5% | 0–2% | 1% |
| Fluorescent Whitening Agent | 0–2% | 0–1% | 0.5% |
| Builder | 0–10% | 0–5% | 1% |
| pH Adjusting Salt | 0–10% | 0–5% | 0.5% |
| Viscosity Modifier | 0–10% | 0–5% | 3% |
| Dye/Colorant | 0–0.5% | 0–0.5% | 0–0.5% |
| Fragrance | 0–0.5% | 0–0.5% | 0–0.5% |
| Water | 0–95% | q.s. to 100% | q.s. to 100% |

In the above system, Part A and Part B would be stored in separate compartments or chambers to prevent intermixing (cross-contamination or premature reaction). At time of use, preferably equal proportions (or, in an alternative embodiment, in a fixed ratio) of Part A and Part B would be combined by the user (for example, by co-metering the two liquid formulations) and poured into, for example, a washing apparatus. Ingredients would be placed into the appropriate Part A or Part B so as to achieve the optimum physical and chemical storage stability, and individual ingredient stability. Additionally, by separate storage in a multiple delivery system, oxidation-sensitive materials, such as alkaline proteases, could be stored in an alkaline environment, while the acid-stable ingredients, such as hydrogen peroxide and the MMA compounds, could be stored in an acidic environment. Finally, as the MMA compound/hydrogen peroxide combination works best in an alkaline environment, upon dispensing into the alkaline wash water, the best performance conditions would be achieved upon such dispensing.

In the next Example, a preferred concentrated laundry additive formulation is disclosed which is within the scope of the invention.

Example 4
Concentrated Laundry Additive

| Ingredient | Wt. % Active | Commercial Material |
|---|---|---|
| Anionic Surfactant | 8% | $C_{12-15}$ Alkylbenzene Sulfonate |
| Nonionic Surfactant | 5% | Neodol 25-7 |
| Hydrogen Peroxide | 5% | Cosmetic Grade Peroxide |
| MMA Compound | 3.5% | MMAMS* |
| Fluorescent Whitening Agent | 0.2% | Tinopal CBS-X |
| Builder | 0.5% | Sodium Chloride |
| Preservative | 0.02% | Butylated Hydroxytoluene |

-continued

| Ingredient | Wt. % Active | Commercial Material |
|---|---|---|
| Chelating Agent | 2% | Dequest 2010 |
| pH Adjusting Agent | 1% | Sulfuric Acid |
| Viscosity/Phase Modifier | 1% | Triethanolamine |
| Dye | 0–0.5% | Various Vendors |
| Fragrance | 0–0.5% | " |
| D.I. Water | q.s. | |

*Not a presently commercially available material.

In the next Example, an especially preferred two part concentrated laundry additive is disclosed which is within the invention.

Example 5
Two Part Concentrated Laundry Additive

| Ingredient | Wt. % | Commercial Material |
|---|---|---|
| Part A | | |
| Anionic Surfactant | 10.0% | $C_{12-15}$ Alkylbenzene Sulfonate |
| Nonionic Surfactant | 8.0% | Neodol 25-12 |
| Hydrogen Peroxide | 6.0% | Cosmetic Grade |
| MMA | 2.0% | MMAMS |
| Preservative | 0.2% | Butylated Hydroxytoluene |
| Chelating Agent | 2% | Dequest 2006 |
| pH Adjusting Salt | 1% | Phosphoric Acid |
| Dye/Colorant | 0–0.5% | Various Vendors |
| Water | q.s. to 100% | |
| Part B | | |
| Nonionic Ethoxylated Surfactant | 6.5% | Neodol 25-7 |
| Nonionic Surfactant | 1.5% | Barlox 12 |
| Enzymes | 1% | Novo Protease |
| Fluorescent Whitening Agent | 0.5% | Tinopal AMS |
| Builder | 1.0% | Sodium Chloride |
| pH Adjusting Salt | 0.5% | Sodium Hydroxide |
| Viscosity Modifier | 3% | Polyethylene Glycol |
| Dye/Colorant | 0–0.5% | Various Vendors |
| Fragrance | 0–0.5% | Various Vendors |
| Water | q.s. to 100% | |

In Examples 6–8 below, exemplary dual chamber hard surface cleaner formulations were created and tested for stain removal performance against a laboratory mildew stain (*Aspergillus niger*). The stain was applied to bisque tiles (unglazed ceramic tiles to essentially mimic bathroom grout). A proprietary Minolta colorimeter was used to determine cleaning performance. To calibrate the calorimeter, a clean tile was used, and then the stained tile was read. Then, after the inventive cleaning composition was applied, the colorimeter read the tiles, and the readout would indicate % stain removal at various elapsed time intervals. In the Examples, the pH level was varied to compare performance at differing pH levels. Part A contained the MMA compound, hydrogen peroxide and a buffer. Part B contained an alkaline material.

Examples 6–8

| Ingredient | Example 6 | | | Example 7 | | | Example 8 | | |
| --- | --- | --- | --- | --- | --- | --- | --- | --- | --- |
| | A | B | Blend | A | B | Blend | A | B | Blend |
| $H_2O_2$ | 4.04 | | 2.02 | 4.04 | | 2.02 | 4.04 | | 2.02 |
| MMAMS | 10 | | 5 | 10 | | 5 | 10 | | 5 |
| $H_2SO_4$ | 2.43 | | 1.21 | 0.89 | | 0.45 | 0.89 | | 0.45 |
| NaOH | | | | | | | | 1 | 0.5 |
| $Na_2CO_3$ | | 10 | 5 | | 10 | 5 | | 10 | 5 |
| $H_2O$ | balance | balance | balance | balance | balance | balance | balance | balance | balance |
| pH | | 7.6 | | | 8.5 | | | 9.5 | |
| Molar Ratio of $H_2O_2$: MMAMS | | 3 | | | 3 | | | 3 | |

The formulations of Examples 6–8 were tested for performance in stain removal as described above. It was found that, at lower pH's, the formulation—at equal dosages of active, i.e., at a 3:1 molar ratio of $H_2O_2$:MMAMS—had better stain removal performance at lower pH. This is graphically depicted in FIG. 1, in which the Y axis is % stain removal, the X axis is time in seconds. The data depicted have been adjusted for 100% stain removal by focusing on the area where the inventive bleaching formulation was applied.

It is to be understood that while the invention has been described above in conjunction with preferred specific embodiments, the description and examples are intended to illustrate and not limit the scope of the invention, which is defined by the appended claims.

We claim:

1. A liquid cleaning composition including a compound with the structure of Formula I

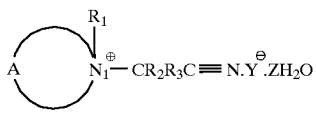

wherein A is a saturated ring formed by five atoms in addition to the $N_1$ atom, the five saturated ring atoms being four carbon atoms and a heteroatom, the substituent $R_1$ bound to the $N_1$ atom of the Formula I structure is (a) a $C_{1-8}$ alkyl or alkoxylated alkyl where the alkoxy is $C_{2-4}$, (b) a $C_{4-24}$ cycloalkyl, (c) a $C_{7-24}$ alkylaryl, (d) a repeating or nonrepeating alkoxy or alkoxylated alcohol, where the alkoxy unit is $C_{2-4}$, or (e) —$CR_2 R_3 C \equiv N$ where $R_{2'}$ and $R_{3'}$ are each H, a $C_{1-24}$ alkyl, cycloalkyl, or alkylaryl, or a repeating or nonrepeating alkoxyl or alkoxylated alcohol where the alkoxy unit is $C_{2-4}$, the $R_2$ and $R_3$ substituents are each H, a $C_{1-24}$ alkyl, cycloalkyl, or alkylaryl, or a repeating or nonrepeating alkoxyl or alkoxylated alcohol where the alkoxy unit is $C_{2-4}$, and wherein Y is an counterion and Z is in the range of 0 to 10.

2. The liquid composition of claim 1 wherein the counterion is either alkylsulfate, bisulfate, sulfate, tosylate or mixtures thereof.

3. The liquid composition of claim 1 wherein said liquid includes an inert, nonreactive liquid.

4. The liquid composition of claim 3 wherein said liquid is selected from the group consisting of water, organic solvents and mixtures thereof.

5. The liquid composition of claim 1 wherein said liquid comprises a nonaqueous liquid.

6. The liquid composition of claim 5 wherein said nonaqueous liquid comprises liquid nonionic surfactants, organic solvents, or mixtures thereof.

7. The liquid compositions of claim 1 wherein $R_1$ is a $C_{1-4}$ alkyl.

8. The liquid composition of claim 7 wherein $R_1$ is methyl.

9. The liquid composition of claim 8 wherein $R_2$ and $R_3$ are both hydrogen.

10. The liquid composition of claim 9 wherein the heteroatom is oxygen or sulphur.

11. The liquid composition of claim 10 wherein the heteroatom is oxygen.

* * * * *